(12) United States Patent
Della Grotta

(10) Patent No.: US 7,007,697 B1
(45) Date of Patent: Mar. 7, 2006

(54) RESPIRATION ASSISTING AND SNORE REDUCING APPARATUS

(76) Inventor: Nicholas Della Grotta, 9160 NW. 56 St., Cooper City, FL (US) 33328

( * ) Notice: Subject to any disclaimer, the term of this patent is extended or adjusted under 35 U.S.C. 154(b) by 0 days.

(21) Appl. No.: 10/462,367

(22) Filed: Jun. 16, 2003

(51) Int. Cl.
*A62B 18/08* (2006.01)

(52) U.S. Cl. .................. 128/848; 128/860; 128/859

(58) Field of Classification Search ............ 128/848, 128/859–860, 863, 201.26, 200.26, 206.26, 128/206.28, 206.29; 602/902; 606/234–236
See application file for complete search history.

(56) References Cited

U.S. PATENT DOCUMENTS

| | | | |
|---|---|---|---|
| 5,427,117 A | 6/1995 | Thornton | 128/848 |
| 5,720,302 A | 2/1998 | Belfer | 128/848 |
| 5,810,013 A | 9/1998 | Belfer | 128/848 |
| 5,921,241 A | 7/1999 | Belfer | 128/848 |
| 6,427,696 B1 | 8/2002 | Stockhausen | 128/848 |
| 6,679,257 B1 * | 1/2004 | Robertson et al. | 128/204.18 |
| 2005/0092331 A1 * | 5/2005 | D'Agosto | 128/859 |

* cited by examiner

*Primary Examiner*—Henry Bennett
*Assistant Examiner*—Dinnatia Doster-Greene
(74) *Attorney, Agent, or Firm*—Frank L. Kubler

(57) ABSTRACT

A respiration assisting apparatus is provided, including a first anchor structure for fitting between the teeth and the cheek of a first side of a user mouth to retain the apparatus in operational position; and a lip separating structure extending forwardly from the first anchor structure for passing between and separating the lips of a user. The first anchor structure and lip separating structure preferably include venting openings for permitting oxygen to reach adjacent mouth tissue. The first anchor structure preferably includes an upright first anchor panel. The lip separating structure preferably includes a projection channel extending longitudinally forward from the first anchor structure. The respiration assisting apparatus optionally additionally includes a tongue suppressing bridge.

17 Claims, 2 Drawing Sheets

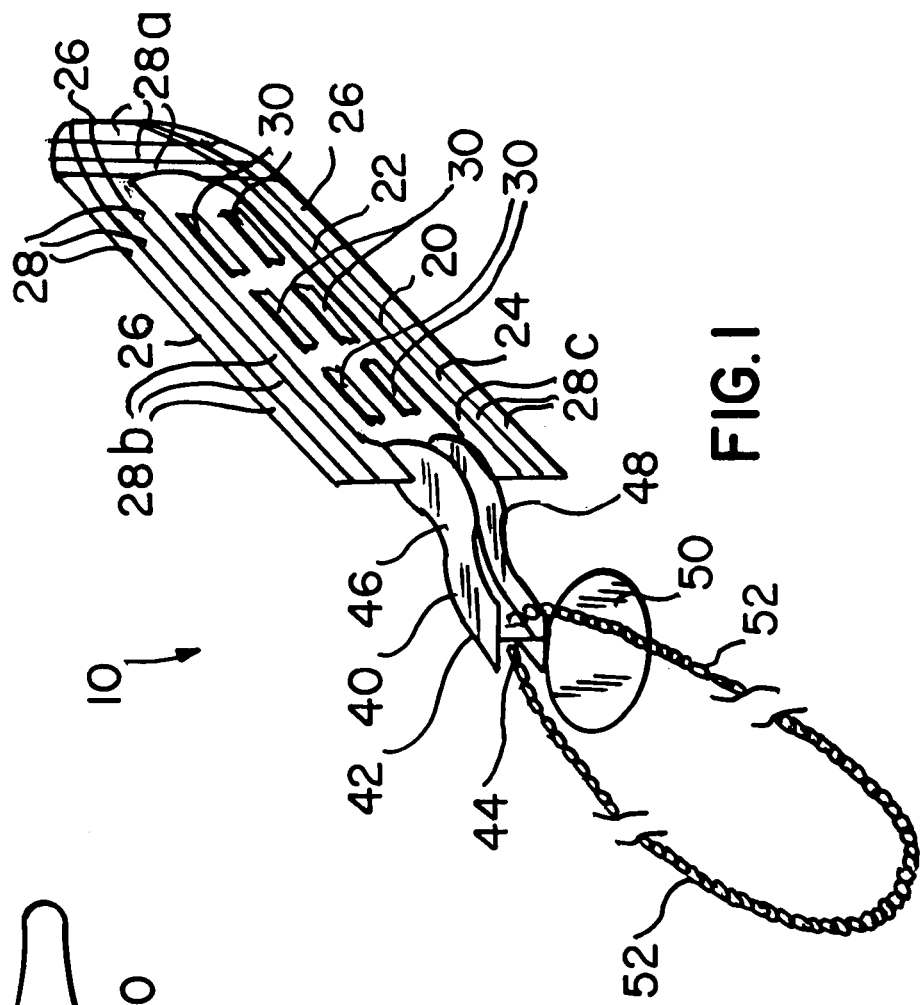
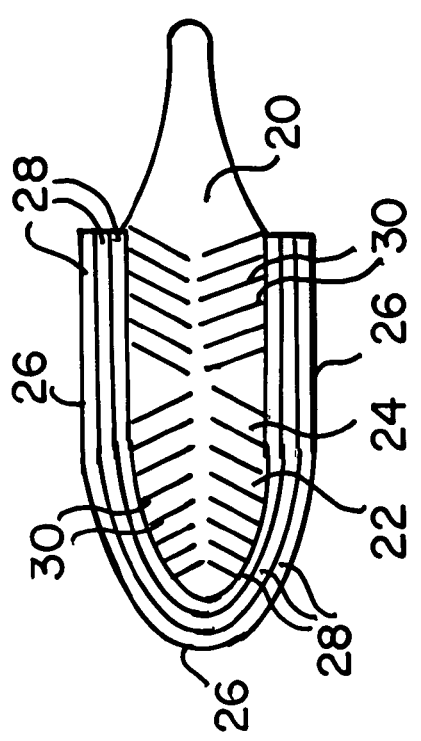

RESPIRATION ASSISTING AND SNORE REDUCING APPARATUS

BACKGROUND OF THE INVENTION

1. Field of the Invention

The present invention relates generally to the field of devices for improving respiration and preventing snoring. More specifically the present invention relates to a respiration assisting apparatus for placement in a user mouth to separate the lips and optionally also open a breathing passageway between the tongue and the roof of the mouth, so that persons having nasal congestion or other respiration inhibiting condition such as a deviated septum can breath more freely, especially while sleeping, and so that snoring is minimized. The apparatus includes a cheek first anchor structure which is fitted mouth between the teeth and the adjacent cheek on a first side of the user mouth to retain the apparatus in operation position, and a lip separating structure extending from the first anchor structure between and outward from the user lips, holding lips apart. The first anchor structure and the lip separating structure both preferably have venting openings to permit oxygen to reach cheek tissue adjacent to the apparatus. The first anchor structure preferably takes the form of an upright first anchor panel having smooth first anchor panel surfaces and a generally elliptical first anchor panel perimeter. The lip separating structure preferably takes the form of a projection channel having an upright channel web and laterally extending channel side walls and the projection channel preferably opens toward the center of the user lips so that respiration air can flow longitudinally through the interior of the channel even if the lips close fully around the channel exterior.

A second embodiment of the apparatus has the elements of the first and additionally includes a tongue suppressing bridge for extending laterally from the first anchor structure between upper and lower sets of user teeth on a first side of a user mouth, between the user tongue and roof of the mouth and between upper and lower sets of user teeth on the second side of the user mouth and connects to a second anchor structure between the user cheek and adjacent teeth on a second side of the user mouth. The tongue suppressing bridge includes a central air passing segment which either is spaced downwardly from the roof of the user mouth to permit respiration air to pass over the bridge and alternatively or additionally includes at least one air flow bridge opening for respiration air to flow through the bridge.

2. Description of the Prior Art

There have long been devices for preventing or minimizing snoring.

Stockhausen, U.S. Pat. No. 6,427,696, issued on Aug. 6, 2002, discloses an anti-snoring device having a cover plate with a curved perimeter and being bowed toward its center to define a concave cover plate side and a convex cover plate side, and which is insertable between the lips and teeth of a person to cover tooth spaces. The concave side includes a mandibularly directed projection as well as a palatally directed projection which, when the device is inserted into the mouth, hook behind the teeth of the upper and lower jaws. The anti-snoring device is formed of material which is plasticizable so that tongue pressure or finger pressure can press the cover plate and projection firmly against the tooth surfaces. The invention further relates to a method for molding the anti-snoring device.

Thornton, U.S. Pat. No. 5,427,117, issued on Jun. 27, 1995, reveals an apparatus for prevention of snoring and improved breathing during sleep. Thornton includes upper and lower channel members which are laterally curved into matching U-shapes to follow the curvature of upper and lower sets of user teeth. The channels contain a deformable material to receive impressions of the individual user teeth and remain removably fixed on the upper and lower sets of teeth, the upper channel having a downwardly extending post which fits behind the lower channel to brace the lower channel and user jaw forwardly to prevent snoring.

Belfer, U.S. Pat. No. 5,720,302, issued on Feb. 24, 1998, is one of three Belfer patents teaching an anti-snoring device having an external shield. Belfer includes a channel member laterally curved to follow a general U-shape for receiving user teeth, the channel containing tooth receiving areas separated by ribs, and an elongated strip extending forwardly from the connected channel forward end fitted with an upright shield which fits over the outside facial surfaces around a user mouth for preventing the lower jaw from drifting inferiorly and posteriorly during sleep. Belfer, U.S. Pat. No. 5,810,013, issued on Sep. 22, 1998, and Belfer, U.S. Pat. No. 5,921,241, issued on Jul. 13, 1999 cover essentially the same oral shield disclosed in U.S. Pat. No. 5,720,302, except that they include an extension member fixedly connected to the front of the channel and a connecting member slidably connected to the oral shield having an opening for slidably receiving the extension member, and an upright telescoping shield mounting member so that the shield position relative to the channel can be adjusted to fit the individual wearer.

It is thus an object of the present invention to provide a respiration assisting and snore suppressing apparatus which separates user lips to maintain a free flow of respiration air while a user is sleeping.

It is another object of the present invention to provide such an apparatus which optionally maintains a respiration air passageway between the user tongue and roof of the user mouth.

It is still another object of the present invention to provide such an apparatus which is comfortable.

It is finally an object of the present invention to provide such an apparatus which is safe to use and inexpensive to manufacture.

SUMMARY OF THE INVENTION

The present invention accomplishes the above-stated objectives, as well as others, as may be determined by a fair reading and interpretation of the entire specification.

A respiration assisting apparatus is provided, including a first anchor structure for fitting between the teeth and the cheek of a first side of a user mouth to retain the apparatus in operational position; and a lip separating structure extending forwardly from the first anchor structure for passing between and separating the lips of a user. The first anchor structure preferably includes at least one venting opening for permitting oxygen to reach adjacent mouth tissue. The lip separating structure preferably includes at least one venting opening for permitting oxygen to reach adjacent mouth tissue. The first anchor structure preferably includes an upright first anchor panel. The upright first anchor panel preferably includes a smooth first anchor panel surface and a substantially rounded first anchor panel perimeter. The lip separating structure preferably includes a projection channel extending longitudinally forward from the first anchor structure and having an upright channel web and laterally extending channel side walls, so that respiration air can flow longitudinally through the interior of the projection channel.

The respiration assisting apparatus optionally additionally includes a tongue suppressing bridge extending laterally from the first anchor structure for fitting between upper and lower sets of user teeth on a first side of a user mouth, between the tongue of a user and the roof of a user mouth and between upper and lower sets of user teeth on a second side of a user mouth. The respiration assisting apparatus preferably still additionally includes a second anchor structure for placement between a user cheek and adjacent user teeth on a second side of a user mouth, where the tongue suppressing bridge connects to the second anchor structure. The tongue suppressing bridge preferably includes flat bite segments for extending between upper and lower sets of user teeth while permitting upper and lower sets of user teeth to substantially close together. The tongue suppressing bridge preferably includes a central air passing segment. The tongue suppressing bridge optionally is configured to be spaced downwardly from the roof of a user mouth to permit respiration air to pass over the tongue suppressing bridge. The tongue suppressing bridge optionally includes at least one bridge air flow port through which respiration air can flow.

The second anchor structure preferably includes an upright second anchor panel. The second anchor panel preferably has a smooth second anchor panel surface and a substantially rounded second anchor panel perimeter. The second anchor structure preferably includes at least one venting opening for permitting oxygen to reach adjacent mouth tissue. The apparatus preferably is formed at least in part of a thermoplastic known as THEMOLYN-PEDILON or POLYSPLINT™.

BRIEF DESCRIPTION OF THE DRAWINGS

Various other objects, advantages, and features of the invention will become apparent to those skilled in the art from the following discussion taken in conjunction with the following drawings, in which:

FIG. 1 is a perspective view of the first embodiment of the inventive respiration assisting apparatus including the first anchor structure and lip separating structure.

FIG. 2 is a side view a second variation of the first anchor structure having continuous, non-segmented perimeter strips.

DETAILED DESCRIPTION OF THE PREFERRED EMBODIMENTS

Figure 3:
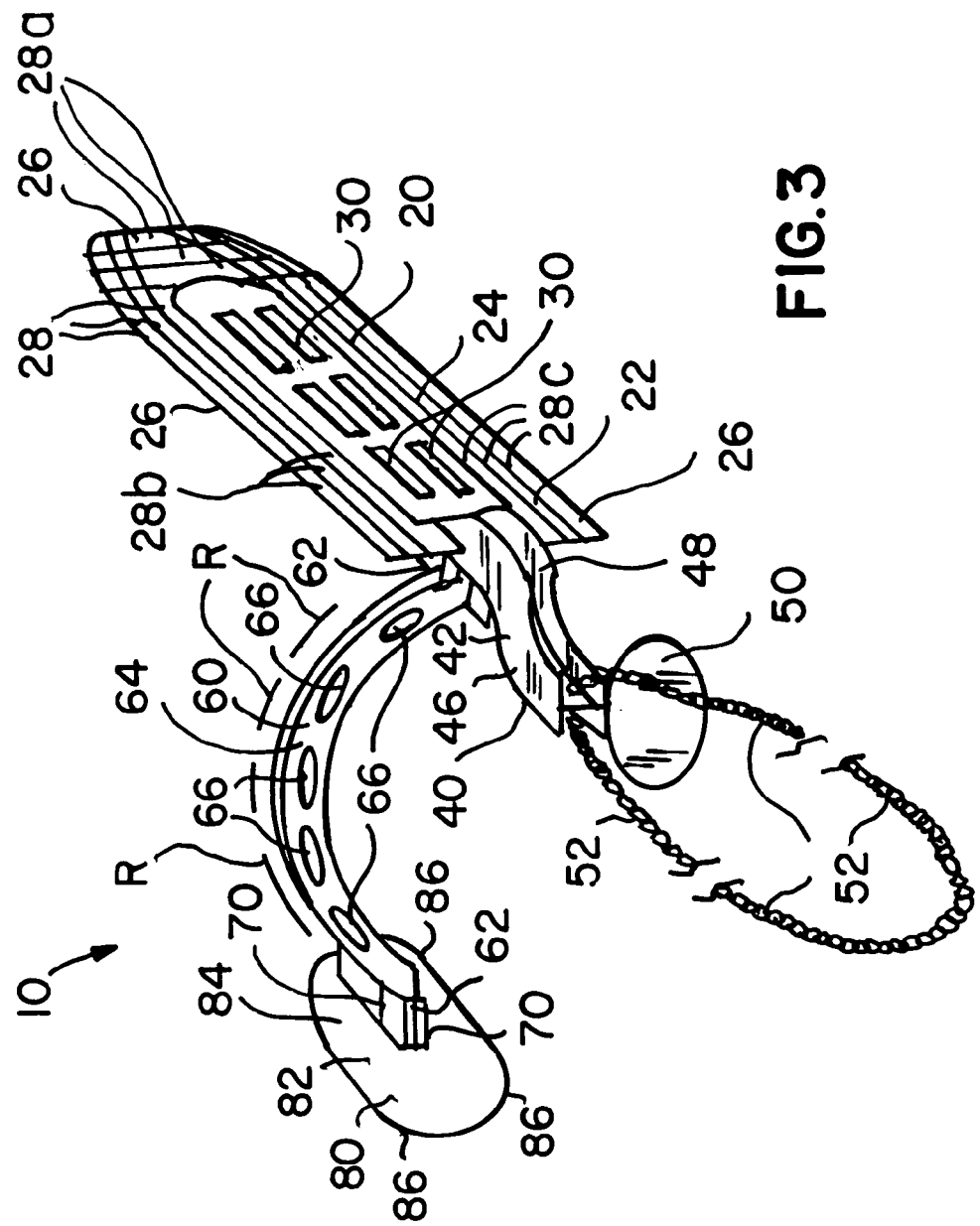
FIG. 3 is a side perspective view of the second preferred embodiment of the apparatus, having the tongue suppressing bridge and second anchor structure.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–2, a respiration assisting apparatus 10 is disclosed including a first anchor structure 20 which is fitted between the teeth and the adjacent cheek on a first side of a user mouth to retain apparatus 10 in operational position, and a lip separating structure 40 extending from the first anchor structure 20 between and outwardly from the user lips, holding lips apart. The first anchor structure 20 and the lip separating structure 40 both preferably have venting openings 30 to permit oxygen to reach cheek tissue adjacent to apparatus 10.

The first anchor structure 20 preferably takes the form of an upright first anchor panel 22 having smooth first anchor panel surfaces 24 and a generally elliptical first anchor panel perimeter 26. The first anchor structure 20 preferably includes a radial series of individually removable perimeter strips 28 for discretionary and selective removal to reduce the height and length size of the first anchor panel 22 to comfortably fit relatively smaller user mouths. See FIGS. 1 and 2. These perimeter strips 28 may be generally U-shaped, each extending along the first anchor panel 22 upper end, rearward end and lower end, and preferably are separated from each other either by marked lines, for removal by scissor cutting, by tear guiding grooves or by a closely spaced series of tear guiding perforations, for removal by tearing. For another variation, segmented perimeter strips 28 are provided, each with a separately removable strip rear segment 28a, strip upper segment 28b and strip lower segment 28c, so that either the entire perimeter strips 28 or only selected segments 28a, 28b or 28c can be removed to not only custom size the first anchor panel 22 but also to custom shape the first anchor panel 22 to comfortably fit the individual mouth. See FIG. 1. The venting openings 30 in the first anchor panel 22 preferably have the configuration of segments of elongate slots, as shown in FIG. 1, or are angled slots, as shown in FIG. 2.

The lip separating structure 40 preferably includes a projection channel 42 having an upright channel web 44 and channel side walls 46 and 48 extending laterally in two opposing directions so that respiration air can flow longitudinally through the interior of the channel 40, even if the user lips happen to close fully around the channel 40 exterior. Projection channel 42 preferably opens toward the center of the user lips to extend the opening of parted user lips. A safety abutment structure 50 preferably extends laterally from the projection channel 42 to abut the user face outside the user mouth to prevent accidental swallowing of the apparatus 10. Alternative or additionally to the safety abutment structure 50, a safety chain 52 preferably is provided which is secured to the projection channel 42 forward end, outside the user mouth. See FIGS. 1 and 3. The safety chain 52 preferably is loop shaped for fitting around the user neck to prevent the apparatus 10 from sliding back into the user mouth, and alternatively is secured to an article of user clothing and may or may not be loop shaped.

Second Preferred Embodiment

A second embodiment of apparatus 10 has the elements of the first embodiment and additionally includes a tongue suppressing bridge 60 for extending laterally from the first anchor structure 20 between upper and lower sets of user teeth on a first side of a user mouth, between the user tongue and roof R of the mouth and between upper and lower sets of user teeth on a second side of the user mouth and connects to a second anchor structure 80 for placement between the cheek and the teeth on a second side of the user mouth. See FIG. 3. The tongue suppressing bridge 60 preferably includes flat bite segments 62 for extending between upper and lower sets of the user teeth and permitting the teeth to substantially close together, and includes a central air passing segment 64 which is configured to be spaced downwardly from the roof R of a user mouth to permit respiration air to pass over the bridge 60. Alternatively or additionally, the bridge 60 includes at least one bridge air flow port 66 through which respiration air can flow. The second anchor structure 80 preferably is also an upright second anchor panel 82 having smooth second anchor panel surfaces 84 and a substantially elliptical second anchor panel perimeter 86 and venting openings 30. Upper and lower surfaces of the bite segments 62 optionally are fitted with deformable cushioning pads 70 to protect user teeth against damage from unconscious grinding of teeth, particularly while the user is sleeping.

Both embodiments of apparatus 10, including the cushioning pads 70, preferably are formed of a thermoplastic known as THEMOLYN-PEDILON or POLYSPLINT™. Furthermore, both embodiments preferably are provided in various sizes and proportions to comfortably fit into child and adult mouths of virtually all sizes and shapes.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A respiration assisting apparatus, comprising:
   a first anchor structure for fitting between the teeth and the cheek of a first side of a user mouth to retain the apparatus in operational position;
   and a lip separating structure extending forwardly from said first anchor structure for passing between and separating the lips of a user, said lip separating structure extending longitudinally forward from said first anchor structure to pass adjacent to user teeth and having a laterally open separating structure upright portion, such that respiration air can flow both laterally against and longitudinally along said lip separating structure.

2. The respiration assisting apparatus of claim 1, wherein said first anchor structure comprises at least one venting opening for permitting oxygen to reach adjacent mouth tissue.

3. The respiration assisting apparatus of claim 1, wherein said lip separating structure comprises at least one venting opening for permitting oxygen to reach adjacent mouth tissue.

4. The respiration assisting apparatus of claim 1, wherein said first anchor structure comprises an upright first anchor panel.

5. The respiration assisting apparatus of claim 4, wherein said upright first anchor panel comprises a smooth first anchor panel surface and a substantially rounded first anchor panel perimeter.

6. A respiration assisting apparatus, comprising:
   a first anchor structure for fitting between the teeth and the cheek of a first side of a user mouth to retain the apparatus in operational position;
   and a lip separating structure extending forwardly from said first anchor structure for passing between and separating the lips of a user, said lip separating structure comprising a laterally open projection channel extending longitudinally forward from said first anchor structure and having an upright channel web and laterally extending channel side walls, such that said channel is laterally open and respiration air can flow laterally into and longitudinally through the interior of said projection channel.

7. The respiration assisting apparatus of claim 1, additionally comprising a tongue suppressing bridge extending laterally from said first anchor structure for fitting between upper and lower sets of user teeth on a first side of a user mouth, between the tongue of a user and the roof of a user mouth and between upper and lower sets of user teeth on a second side of a user mouth.

8. The respiration assisting apparatus of claim 7, additionally comprising a second anchor structure for placement between a user cheek and adjacent user teeth on a second side of a user mouth, wherein said tongue suppressing bridge connects to said second anchor structure.

9. The respiration assisting apparatus of claim 7, wherein said tongue suppressing bridge comprises flat bite segments for extending between upper and lower sets of user teeth while permitting upper and lower sets of user teeth to substantially close together.

10. The respiration assisting apparatus of claim 9, wherein said tongue suppressing bridge comprises a central air passing segment.

11. The respiration assisting apparatus of claim 9, wherein said tongue suppressing bridge is configured to be spaced downwardly from the roof of a user mouth to permit respiration air to pass over said tongue suppressing bridge.

12. The respiration assisting apparatus of claim 9, wherein said tongue suppressing bridge comprises at least one bridge air flow port through which respiration air can flow.

13. The respiration assisting apparatus of claim 8, wherein said second anchor structure comprises an upright second anchor panel.

14. The respiration assisting apparatus of claim 13, wherein said second anchor panel has a smooth second anchor panel surface and a substantially rounded second anchor panel perimeter.

15. The respiration assisting apparatus of claim 8, wherein said second anchor structure comprises at least one venting opening for permitting oxygen to reach adjacent mouth tissue.

16. The respiration assisting apparatus of claim 1, wherein said apparatus is formed at least in part of THEMOLYN-PEDILON.

17. A respiration assisting apparatus, comprising:
    an anchor structure for fitting between the teeth and the cheek of a first side of a user mouth to retain the apparatus in operational position, said anchor structure having a radial series of individually removable perimeter strips for reducing the height and length of said anchor structure to custom size said anchor structure to fit a specific user mouth;
    and a lip separating structure extending forwardly from said anchor structure for passing between and separating the lips of a user, said lip separating structure extending longitudinally forward from said anchor structure to pass adjacent to user teeth and having a laterally open separating structure upright portion, such that respiration air can flow both laterally against and longitudinally along said lip separating structure.

* * * * *